(12) United States Patent
Derkx et al.

(10) Patent No.: US 12,220,222 B2
(45) Date of Patent: Feb. 11, 2025

(54) DEVICE AND METHOD FOR DETERMINING AND/OR MONITORING THE RESPIRATORY EFFORT OF A SUBJECT

(71) Applicant: KONINKLIJKE PHILIPS N.V., Eindhoven (NL)

(72) Inventors: Rene Martinus Maria Derkx, Eindhoven (NL); Sandrine Magali Laure Devot, London (GB); Jakob Van De Laar, Oosterhout (NL); Alan James Davie, Milton (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 78 days.

(21) Appl. No.: 15/540,302

(22) PCT Filed: Jan. 14, 2016

(86) PCT No.: PCT/EP2016/050589
§ 371 (c)(1),
(2) Date: Jun. 28, 2017

(87) PCT Pub. No.: WO2016/120074
PCT Pub. Date: Aug. 4, 2016

(65) Prior Publication Data
US 2017/0360329 A1    Dec. 21, 2017

(30) Foreign Application Priority Data

Jan. 28, 2015    (EP) .................................... 15152773

(51) Int. Cl.
*A61B 5/00*    (2006.01)
*A61B 5/024*    (2006.01)
(Continued)

(52) U.S. Cl.
CPC .......... *A61B 5/085* (2013.01); *A61B 5/02438* (2013.01); *A61B 5/0816* (2013.01);
(Continued)

(58) Field of Classification Search
CPC ..... A61B 5/0488; A61B 5/6833; A61B 5/085; A61B 5/04238; A61B 5/0816
See application file for complete search history.

(56) References Cited

U.S. PATENT DOCUMENTS 6,514,218 B2 * 2/2003 Yamamoto ............. A61B 5/103
600/587
6,588,423 B1 * 7/2003 Sinderby ............ A61B 5/04884
128/204.23
(Continued)

FOREIGN PATENT DOCUMENTS

CA         2914494 A1    12/2014
JP      2010119822 A      6/2010
(Continued)

OTHER PUBLICATIONS

Respiratory Rate and Flow Waveform Estimation from Tri-axial Accelerometer Data (Year: 2010).*
(Continued)

*Primary Examiner* — Sana Sahand

(57) ABSTRACT

A device and method for determining and/or monitoring the respiratory effort of a subject are presented. The device comprises a receiving unit for receiving a posture signal of the subject, a breathing signal of the subject, and an electromyography signal of the subject; and a processing unit for determining an electromyography signal based on the posture signal and the breathing signal and for deriving the respiratory effort based on the determined electromyography signal.

18 Claims, 3 Drawing Sheets

(51) Int. Cl.
*A61B 5/08* (2006.01)
*A61B 5/085* (2006.01)
*A61B 5/113* (2006.01)
*A61B 5/296* (2021.01)
*A61B 5/389* (2021.01)

(52) U.S. Cl.
CPC .............. *A61B 5/113* (2013.01); *A61B 5/296* (2021.01); *A61B 5/389* (2021.01); *A61B 5/6823* (2013.01); *A61B 5/6833* (2013.01); *A61B 5/7203* (2013.01); *A61B 5/7278* (2013.01); *A61B 2560/0412* (2013.01); *A61B 2562/0209* (2013.01); *A61B 2562/0219* (2013.01); *A61B 2562/06* (2013.01); *A61B 2562/18* (2013.01)

(56) References Cited

U.S. PATENT DOCUMENTS

| | | | |
|---|---|---|---|
| 8,412,331 | B2 | 4/2013 | Tehrani et al. |
| 8,591,430 | B2 | 11/2013 | Amurthur et al. |
| 2004/0249299 | A1 | 12/2004 | Cobb |
| 2005/0115561 | A1* | 6/2005 | Stahmann ............ A61N 1/3627 128/200.24 |
| 2005/0209511 | A1* | 9/2005 | Heruth .................. A61B 5/1116 600/301 |
| 2006/0149334 | A1* | 7/2006 | Tehrani ................ A61N 1/3601 607/42 |
| 2006/0282131 | A1* | 12/2006 | Caparso ............... A61N 1/3601 607/62 |
| 2007/0032733 | A1* | 2/2007 | Burton ............... A61B 5/02405 600/509 |
| 2007/0255184 | A1* | 11/2007 | Shennib ............... A61B 5/0006 600/591 |
| 2007/0270671 | A1 | 11/2007 | Gal |
| 2010/0234699 | A1* | 9/2010 | Lanfermann ...... A63B 24/0006 600/301 |
| 2011/0004081 | A1 | 1/2011 | Addison et al. |
| 2011/0257554 | A1* | 10/2011 | Banet .................. A61B 5/0809 600/536 |
| 2012/0029375 | A1 | 2/2012 | Lane et al. |
| 2012/0245482 | A1 | 9/2012 | Bolser |
| 2012/0253156 | A1* | 10/2012 | Muhlsteff .......... A61B 5/02416 600/324 |
| 2013/0116520 | A1* | 5/2013 | Roham ................ A61B 5/6833 600/324 |
| 2013/0310699 | A1* | 11/2013 | Hart ..................... A61B 5/0488 600/484 |
| 2013/0345585 | A1* | 12/2013 | Gopal Samy .......... A61B 5/024 600/529 |
| 2014/0128778 | A1* | 5/2014 | Chan .................... A61B 5/1116 600/595 |
| 2014/0180029 | A1 | 6/2014 | Hansmann |
| 2014/0276167 | A1 | 9/2014 | Dasgupta et al. |
| 2015/0084860 | A1* | 3/2015 | Aleem .................... G06F 3/017 345/156 |
| 2015/0366504 | A1* | 12/2015 | Connor ................ A61B 5/6804 600/301 |
| 2016/0000376 | A1* | 1/2016 | Murray ................ A61B 5/6833 600/534 |

FOREIGN PATENT DOCUMENTS

| | | |
|---|---|---|
| JP | 2014514032 A | 6/2014 |
| WO | 2009031064 A2 | 3/2009 |
| WO | 2013136264 A1 | 9/2013 |
| WO | WO-2015153837 A1 * | 10/2015 ........... A61B 5/4836 |

OTHER PUBLICATIONS

P.B. Murphy, et. al., "Chronic obstructive pulmonary disease, Neural respiratory drive as a physiological biomarker to monitor change during acute exacerbations of COPD", Thorax 2010, May 19, 2011 (published online).

E. Hanafin Breslin, et. al., "Respiratory muscle function in patients with chronic obstructive pulmonary disease", Heart & Lung, vol. 24, No. 4, Jul./Aug. 1996, pp. 271-285.

A. Bartolo, et. al., "Analysis of diaphragm EMG signals: comparison of gating vs. subtraction for removal of ECG contamination", Journal of applied physiology, 80(6), pp. 1898-1902, Jun. 1996.

M.L. Duiverman, et.al., "Reproducibility and responsiveness of a non-invsaive EMG technique of the respiratory muscles in COPD patients and in healthy subjects", J. Appl. .Physiol., Dec. 5, 2003.

Serge H. Roy et al., "A Combined sEMG and Accelerometer System for Monitoring Functional Activity in Stroke", Neural Systems and Rehabilitation Engineering, IEEE Transactions on (vol. 17, issue 6, pp. 585-594) Dec. 2009.

* cited by examiner

DEVICE AND METHOD FOR DETERMINING AND/OR MONITORING THE RESPIRATORY EFFORT OF A SUBJECT

CROSS-REFERENCE TO PRIOR APPLICATIONS

This application is the U.S. National Phase application under 35 U.S.C. § 371 of International Application Serial No. PCT/EP2016/050589, filed on 14 Jan. 2016, which claims the benefit of U.S. application Ser. No. 15/152,773.6, filed on 28 Jan. 2015. These applications are hereby incorporated by reference herein.

FIELD OF THE INVENTION

The present invention relates to a device and method for determining and/or monitoring the respiratory effort of a subject. The present invention relates further to an electromyography (EMG) patch. The present invention relates particularly to the measurement of respiratory muscle activity for determining and/or monitoring the respiratory effort of a subject based on the subject's posture signal, breathing signal, and electromyography signal to improve robustness of respiratory effort measurements with EMG.

BACKGROUND OF THE INVENTION

Detection of respiratory effort is important for the assessment and monitoring a number of disorders, including chronic obstructive pulmonary disease (COPD) and asthma. Respiratory effort may be measured by a number of devices including the use of electromyography.

In patients with for example COPD or other respiratory diseases, the assessment of the respiratory muscle activity may be useful to estimate the intensity, timing and duration of patient respiratory effort, as an indicator of the balance between respiratory muscle load and respiratory muscle capacity. It is known that EMG activity from obligate inspiratory muscles relates to the neural respiratory drive (NRD). In COPD patients, during increasing lung hyperinflation as observed during acute exacerbation, there is a change in the balance between respiratory muscle load and capacity, which is reflected in the neural respiratory drive (reduced capacity and/or increased load, resulting in increased NRD).

Respiratory muscle EMG may be used as an indicator of day-to-day deterioration/improvement of a COPD patient when multiple measurements are performed over a number of days, and as a predictor of hospital readmission after discharge as well.

US 2013/0310699 A1 discloses a method of monitoring a patient including measuring neural respiratory drive. The EMG is analyzed during resting tidal breathing, and the peak magnitude of the rectified or root-mean squared EMG trace for each inspiration is estimated.

US 2006/0282131 discloses a system for sensing and controlling respiration. The system is adapted to monitor physiological parameters to detect the incidence of a central respiratory disease. The system includes an implantable medical device, at least one lead and at least one sensor.

US 2013/0116520 discloses a semi-disposable wearable electronic patch for bio-signal monitoring. The patch may include an accelerometer and an amplifier that accommodates various biopotential signals, such as EMG signals.

US 2014/0276167 discloses a patch having e.g. a microphone and an accelerometer sensor for monitoring breathing effort from sports. Other sensors may be placed on the patch, such as micro-electrode arrays capturing electrical and neural signals for anomaly detection.

Main practical problems still reside in the fact that EMG measurements have poor test-retest repeatability. EMG measurements of the same individual, taken at different times, can still be affected by intra-individual variations from various sources that may impair the EMG properties and confuse the clinical interpretation.

SUMMARY OF THE INVENTION

The present invention deals with overcoming the above-mentioned defects of existing devices for determining and/or monitoring the respiratory effort of a subject.

In particular, it is an object of the present invention to provide a simpler, more accurate, and more efficient device and method for determining and/or monitoring the respiratory effort of a subject. Another object of the present invention is the provision of a device for determining and/or monitoring the respiratory effort of a subject which is easy to operate. Still another object resides in the provision of a device for determining and/or monitoring the respiratory effort of a subject which does not disturb the user. Still another object is the provision of a device for determining and/or monitoring the respiratory effort of a subject and a respective method indicating trend values for respiratory effort.

In a first aspect of the present invention a device for determining and/or monitoring the respiratory effort of a subject is provided. The device comprises a receiving unit for receiving a posture signal of the subject, a breathing signal of the subject, and an electromyography signal of the subject; and a processing unit for determining the electromyography signal based on the received posture signal and the received breathing signal and for deriving the respiratory effort based on the determined electromyography signal.

In a further aspect of the present invention a method for determining and/or monitoring the respiratory effort of a subject is provided. Said method comprises receiving a posture signal of the subject, a breathing signal of the subject, and an electromyography signal of the subject; determining and/or monitoring the electromyography signal based on the received posture signal and the received breathing signal; and deriving the respiratory effort based on the determined electromyography signal.

In yet further aspects of the present invention, there are provided a computer program which comprises program code means for causing a computer or processor to perform the steps of the method disclosed herein when said computer program is carried out on the computer or the processor as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, computer program and medium have similar and/or identical preferred embodiments as the claimed device and as defined in the dependent claims.

The present invention therefore overcomes the above-mentioned disadvantages by employing a posture signal, a breathing signal, and an EMG signal of a subject at the same time. EMG signals may be measured by employing conventional EMG electrode patches. Posture signal and breathing signal of the subject may be determined by employing for instance an accelerometer.

Preferably a built-in tri-accelerometer inside the EMG electrode-patch is used. This provides a posture signal, and a breathing signal corresponding to the location of the EMG electrode-patch. In particular, the posture signal provides accurate and reproducible positioning of the subject on a repeated basis, such as a day-to-day basis. Different postures leading to different tension of the muscles and therefore (non respiratory-related) variations in the properties of EMG signal, which may impair the clinical interpretation, may be avoided. In addition, the breathing signal may be used for distinguishing inspiratory activity from expiratory activity of the muscles. As for assessing respiratory effort inspiratory muscle activity is of particular importance, the breathing signal may be employed to indicate a particular phase within a respiration cycle, such as inspiration.

The electromyography signal is determined based on the correct (received) posture signal and the correct (received) breathing signal. Correct posture signal and correct breathing signal reflect that the subject has the correct position and correct point/interval with the breathing cycle for determining and/or monitoring respiratory effort. In addition or alternatively, correct posture signal and correct breathing signal may indicate for repeated measurements that the subject has essentially the same position and/or essentially the same point/interval with the breathing cycle. The respiratory effort may be obtained based on the determined EMG signal. Preferably, the EMG signal is measured/determined independently of the posture signal and breathing signal; the posture and breathing are then used to compute a measure of respiratory effort, i.e. the EMG signal is analyzed/interpreted using the posture signal and breathing signal.

The EMG signal may be furthermore normalized to reduce the variability both within and between subjects. Normalization helps not only accommodate possible measurement set-up differences from day-to-day (such as differences in electrode placement or skin-electrode contact quality, which can alter signal amplitude) but also helps scale the signal for individual variations (e.g. differences in subcutaneous fat distribution that can also alter signal amplitude). Typically, the EMG is normalized to a maximal or submaximal effort at a known level. For instance, the peak magnitude EMG is normalized to a maximum inspiratory manoeuver or a sniff manoeuver. It is then expressed as a percentage of the peak magnitude EMG obtained during the sniff manoeuver. This value is referred to as normalized value of neural respiratory drive (NRD). When multiplied by the respiratory rate, it is reported as neural respiratory drive index (NRDI). These measures can be used as an indicator of deterioration/improvement. Alternatively, the logarithm of the EMG activity ratio (logEMGAR) has also been reported: either the EMG activity during inspiratory threshold load (sub-maximum effort) is normalized to baseline (no inspiratory load), or the EMG activity during exercise is normalized to EMG activity during quiet breathing at rest.

Alternatively, a plurality of EMG signals may be received by the receiving unit and in response to the received posture signal and the received breathing signal an electromyography signal may be selected from the plurality of EMG signals. Hence, several electromyography signals obtained in the wrong posture and/or wrong breathing state are discarded, and only an EMG signal reflecting the correct posture and the correct breathing state is obtained. Accordingly, the device may comprise a receiving unit for receiving a posture signal of the subject, a breathing signal of the subject, and a plurality of electromyography signals of the subject; and a processing unit for determining the electromyography signal based on the received posture signal and the received breathing signal and for deriving the respiratory effort based on the determined electromyography signal.

EMG signals may be measured by employing for instance two EMG electrodes which are preferably located at a second intercostal space symmetrically to the sternum of the patient. Also a ground electrode located at an electrically neutral position on the body, such as bone, may be used to obtain a differential signal between the two EMG electrodes. Preferably, the EMG signals are obtained from the second intercostal space parasternal muscles (i.e. right and left from the midline of the sternum). It will be, however, appreciated that the electrode(s) need not to be placed with respect to the second intercostal space parasternal muscles but may be also placed on other locations of the subject including for instance the diaphragm or scalene of the subject. The two, optionally disposable, EMG electrodes can be coupled, preferably attached, to a single sensor patch. The respiratory effort may be derived from the voltage that is measured across the two EMG electrodes during the inhalation phase. The use of a single patch with two electrodes or two patches with one electrode each in the before mentioned position on the subject's chest has been found to present a robust measurement for repeated, such as day-to-day, assessment of respiratory effort. The voltage measured by EMG electrodes is influenced not only by the depth and rate of breathing (which may be corrected by taking into account the breathing signal), but also some muscular activity not related to breathing, such as body movements and posture of the subject in general. It has been found that these issues may be tackled by introducing an accelerometer residing inside the EMG measurement patch, i.e. determining and/or monitoring the respiratory effort of a subject based on posture signal, breathing signal, and an electromyography signal of a subject at the same time.

Variability in the EMG signal due to non-muscular factors is preferably reduced through at least one of i) using the same electrodes and amplifier for repeated measurement (i.e. same signal conditioning parameters), ii) ensuring consistency in the skin-electrode contact quality and iii) placing the electrodes over the same skin location in consecutive recording sessions.

It will be appreciated that determining and/or monitoring the posture signal and the breathing signal does not necessarily require the use of one or more accelerometers. In addition or alternatively, posture signal and breathing signal may be assed in different ways.

The posture signal and the breathing signal may be also received for instance by a camera. The camera may determine and/or monitor posture and breathing movement of the subject. An evaluation unit configured to determine the correct posture and the correct breathing phase and rate may be further configured to transfer said values to the proposed device. Alternatively, the camera may be only used for determining and/or monitoring correct posture of the subject, whereas breathing rate is determined and/or monitored in a different way, for instance by electrocardiography. The breathing signal may be further determined and/or monitored using any state of the art devices such as a respi-band, a nasal cannula with differential pressure sensor, etc.

The method may be carried out by placing a single electrode patch having two electrodes, or two electrode patches, comprising an accelerometer located the subject, such as the subject's chest. At first, the posture of the patient may be determined. Accordingly the device may provide indication for use telling that the subject should recline for particular values, such as 45 degrees, or should be sitting comfortably with the back supported by the back of the chair. When for instance sitting in a comfortable chair, the user can relax and it will be possible, provided that the subject does not significantly move, that an EMG patch will only determine/measure the electrical activity of the parasternal inspiratory muscles.

Essentially the same position needs to be taken during repeated, such as day-to-day, measurements to have a reliable repeated determining of respiratory effort. The same holds true for a reliable repeated NRD measurement, which may be calculated from the received EMG signal, from which deterioration may be predicted. As the body shape of the subject will not change from day-to-day and the sensor-patch attachment will be also the same from day-to-day, it is possible to measure via the posture signal, using e.g. the accelerometer, whether the posture for the current day is similar, or identical, to the posture of the previous day(s). If this is not the case, this may be communicated to the user, employing for instance a graphical user interface (GUI), that the posture needs to be adapted in order to have a posture that is (sufficiently) similar to the previous day(s). In this way, it may be ascertained that repeated NRD measurements are performed according to the same posture.

The posture signal of the subject comprises determining the position of the subject relative to an axis vertical to the ground. Accordingly, reclining of the upper part of the body is determined and may be compared to an instructed position and angle, e.g. semi-recumbent (head of the bed elevated for an angle, such as 45 degrees) or sitting, with the subject's back resting comfortably on the back of the chair. Preferred angles are in the range from approximately 40 to 60 degrees, such as 40 to 50 degrees, 41 to 49 degrees, 42 to 48 degrees, 43 to 47 degrees, and 44 to 46 degrees. An angle of 45 degrees is preferred. Preferably the posture signal of the subject is determined on a repeated basis, such as a day-to-day basis, wherein an identical or a similar posture is ensured. A similar posture as used herein is directed to a similar angle and refers to an angle with value of ±10 percent or less, preferably ±8 percent or less, ±5 percent or less, ±4 percent or less, ±3 percent or less, ±2 percent or less, and preferably to ±1 percent or less. It is clear that the posture of the subject may be determined not only with respect to the environment, such as the ground, but also with respect to the subject himself/herself by attaching two or more sensors to the subject.

These sensors may be selected from the group consisting of accelerometers, gyroscopes and inertial measurement units (IMU) but are not limited thereto. The sensors are attached to the subject in manner that, for instance vertical, inclination of the subject and therefore the position of the subject's torso may be derived. For instance, two accelerometers may be employed, one attached to the torso of the subject and the other to the head of the subject. Preferably, one of said sensors is employed within an EMG patch. More preferably, one of said sensors is employed within the EMG patch according to the present invention. The use of such sensors may assist in further improving the correct posture/position of the subject by considering for instance the twist of the subject's torso and/or head.

In a next step respiration may be determined using the tri-accelerometer. Since it is known that the subject has a certain reclined position, it is known that an accelerometer moves upwards and tilts in a certain direction (around the fixed axis) during inhalation. Accordingly it is possible to directly relate the upward tilt of the tri-accelerometer to the inspiratory-phase of the patient and detect reliably the start and end of inhalation (which may be based on detection of an essentially similar or same pattern of accelerometer signals). In this way it is possible to separate the inspiratory EMG measurement from the expiratory EMG measurement, and for instance the EMGAR parameter may be calculated. In addition, it is possible to determine for instance the breathing signal (measured via the accelerometer tilt) with respect to the inspiratory muscles activity (measured via the EMG sensor). This phase may be also relevant for prediction of deterioration/improvement of the subject. It is also possible to calculate and to normalize the NRD value with respect to the breathing-depth of the patient.

It is furthermore possible to detect activity of the patient. By computing the 2-norm of the tri-accelerometer data, it is possible to detect a large activity/movement of the patient. In case of a large activity/movement, it is possible to omit the measurement of the NRD value. Furthermore, it is also possible to use the respiration measurement from the accelerometer to detect smaller activity/movement of the subject. For example, when the phases of the tilt (inspiration vs. expiration) of the accelerometer around the correct axis (which is the lateral axis) sufficiently correlate with the EMG measurement (mainly showing inspiratory activity) it is possible to decide that EMG data preliminarily contains inspiratory related signals, such as 90 percent or even 100 percent, and there will be essentially no disturbance from for instance other (non-respiratory related) muscles.

The expression 37 "respiratory effort" as used herein relates to the balance between respiratory muscle load and capacity. Accordingly, "respiratory effort" may correspond to "respiratory muscle activity". The proposed method and device therefore not only enable determining and/or monitoring respiratory effort but also enable determining and/or monitoring respiratory muscle activity. "Respiratory effort" may also relate to neural respiratory drive.

The expressions "neural respiratory drive" and "neural respiratory drive index" as used herein refer to a measure determined as the product of peak EMG activity normalized to the peak EMG activity during an inspiratory sniff maneuver, and in the case of NRDI; multiplied by respiratory rate.

"Respiratory effort", "neural respiratory drive" and "neural respiratory drive index" may be determined from EMG values according to US 2013/0310699 A1 the contents of which are incorporated herein by way of reference in its entirety.

The term "posture signal" as used herein is used for describing the position of the subject. As indicated above the position of the subject may be described relative to the environment or with respect to the subject's posture. Preferably, the position of the subject is described relative to an axis vertical to the ground. Accordingly, the posture signal may include the angle of the upper part of the body with respect to the ground.

The expression "breathing signal" refers to any stage within the full respiratory cycle of a subject, encompassing expiration and inspiration. The "breathing signal" may contain depth, i.e. amplitude, information and/or rate information. Advantageously, a particular point with the stage of the respiratory cycle may be determined and used for repeated measurements. Such a particular point may for instance refer to midway of inhaling when the chest is at half distance between lowermost and topmost position. This permits even more accurate determining and/or monitoring of the subject's respiratory effort.

The wording "electromyography signal" relates to electrical activity produced by intracellular and intercellular neuronal activity. In general, said term refers to electrical potentials generated by the depolarization of muscles.

According to one embodiment of the present invention, the proposed device and method further comprise an accelerometer sensor for measuring the posture signal and the breathing signal of the subject. The accelerometer sensor employed is preferably a tri-axis accelerometer known in the art. The accelerometer preferably comprises a plurality of acceleration axes and a sensor is further adapted to provide a corresponding plurality of acceleration signals. This is a possibility to determine a precise acceleration signal, since a plurality of acceleration directions are measured. The sensor may, for example, comprise a multi-axial accelerometer which is adapted to generate a movement signal indicative of the acceleration along different spatial axes. The multi-axial accelerometer is preferably a tri-accelerometer adapted to generate a movement signal that comprises three accelerometer signals indicative of acceleration along three orthogonal spatial axes, enabling for example measuring tilt and orientation changes of the subject. For example, tri-accelerometers named Bosch BMA 355, ST Microelectronics LIS3DH, LIS2HH12, ST Microelectronics LIS344ALH or Kionix KXM 52 can be used. However, also other kinds of multi-accelerometers can be used for generating accelerometer signal indicative of the acceleration along different spatial axes. The number of accelerometer sensors is not particularly limited and may comprise for instance two, three, four, five different accelerometer sensors. Use of a single sensor is, however, preferred.

According to another embodiment of the present invention the proposed device further comprises an accelerometer sensor for measuring the posture signal and a breathing signal of the subject and an electromyography patch for measuring the electromyography signal of the subject. The accelerometer sensor preferably resides inside the electromyography patch.

Electromyography patches are well known within the art and comprise an electrode material in contact with the subject's skin which is partially embedded in an electrically insulating material, such as plastics, including for instance a rubber material or a silicone material. The EMG patch may be attached to the surface of the skin by adhesion, including for instance adhesion due to the presence of liquid on the skin and patch, due to use of a glue, or due to a vacuum created between patch and skin. It will be appreciated that there are other possibilities for attaching an EMG patch to the skin of a user. The accelerometer sensor preferably resides within the electromyography patch, i.e. within the rubber material being opposite to the skin contacting surface. It will be appreciated, that an accelerometer sensor may be not placed in direct electrical contact with the electrode of the EMG patch. Rather, an isolating layer of e.g. a rubber may be formed between electrode and accelerometer. The accelerometer is preferably surrounded by the rubber material to render the accelerometer and patch watertight. In this manner, disturbances from perspiration may be avoided. Additionally, the patch may be easily cleaned and/or disinfected for next use. The patch may be connected in any suitable manner to the proposed device permitting transferring of a posture signal, breathing signal, and an electromyography signal of the subject. This may be performed by insulated wires.

According to another embodiment of the present invention, the electromyography patch is watertight. This may be obtained by providing a surface of a plastic material, such as silicone or silicone rubber, around the patch. It is clear, that there is a need for a contacting area between the subject's skin and the electrode within the EMG patch. In case the EMG patch also comprises an accelerometer sensor, said sensor is preferably surrounded by the plastic material, such as silicone or silicone rubber, as well.

The proposed device and method for a respiratory effort further feature either the use of two of such EMG patches which are preferably placed at the second intercostal space symmetrically with respect to the sternum of the patient. It is clear that in case two different electrode patches are used, one accelerometer sensor is sufficient for determining the posture signal and the breathing signal of the subject. However, both patches may be provided with an accelerometer sensor, respectively, to provide an average accelerometer signal and, therefore, a more precise posture signal and breathing signal of the subject, respectively. It is, however, preferred to use a single electromyography patch, comprising two electrodes preferably at a distance which is suitable for placing said electrodes above the two second intercostal spaces symmetrically with respect to the sternum of the patient. Such a single patch may also comprise in addition to the two electrodes a single accelerometer sensor, which is preferably attached in the center of the electromyography patch, i.e. at half distance between the two electrodes. Such a patch may be, as discussed above, surrounded by plastics material, such as silicone or silicone rubber, rendering the patch watertight enabling only contact of the two electrodes with the subject's skin.

According to another embodiment of the present invention a plurality of electromyography patches is used. As disclosed above, two, three, four, five, six and more patches may be used. In addition or alternative to the preferred placement position of the patches, i.e. location at the second intercostal space symmetrically with respect to the sternum of the patient, other locations may be used. It will be appreciated, that these locations may also provide the required signal, i.e. electrical activity of parasternal muscle activity. It is furthermore clear that not all of the plurality of electromyography patches need to carry an accelerometer sensor. Preferably, two of the patches employed may carry an accelerometer sensor, respectively. More preferably, a single patch out of the plurality of electromyography patches may carry an accelerometer sensor. Additional electrodes may be used for correcting the determined electromyography signal.

According to another embodiment of the present invention the receiving unit is further arranged for receiving a movement signal of the subject, wherein the processing unit is further configured to determine the electromyography signal based on the movement signal.

The wording "movement signal" as used herein refers to any movement or activity of the subject which is different from breathing. Accordingly, movement refers to any other movement of the subject, including for instance movement of the body, arms etc. The electromyography signal is preferably determined in absence of any other evitable movement, i.e. a quiescent subject or essentially quiescent subject. Such movements may cause non-respiratory muscular activity on the top of the EMG signal from the parasternal muscle, the activity of which needs to be determined. Alternatively or in addition, such different muscle activity may be cancelled, which may be performed by e.g. removing all electrical contributions which are generated at least partially by such movement signals.

According to still another embodiment of the present invention the receiving unit of the proposed device and method is further arranged for receiving a heart rate signal, wherein the processing unit is further configured to correct the determined electromyography signal based on the heart rate signal and to derive the respiratory effort based on the corrected determined electromyography signal.

The heart rate signal may be determined by using an accelerometer. Preferably, the accelerometer of the electrode patch is employed. Alternatively, the heart rate signal may be determining by using any other known method including for instance electrocardiography. As disclosed above, the preferred positioning of the electrode(s) is the positioning of two electrodes at the second intercostal space symmetrically with respect to the sternum of the patient. Accordingly, said electrodes are essentially placed above the subject's heart. In this respect heart activity may falsify the activity of the parasternal muscle activity. Correction may be performed in essentially two ways. The first resides in determining a time interval, wherein essentially no heart activity may be monitored. During such time, the desired determined electromyography signal is also essentially free from artifacts. Alternatively, the EMG signals and heart rate signals may be transformed into the frequency domain (using for instance fast Fourier transforms), or time-frequency domain (using for example Windowed Fourier transforms, Wigner-Ville or wavelet transforms). Peak detectors may be employed for detecting the heart rate signal and including its effect into the EMG signal. A temporal approach may be also employed to track both heart rate signal and EMG signal over time. This could include for example a Kalman filter. These transferred signals may be then further used for removing the heart rate signal from the determined EMG signal.

The proposed device may further comprise an indicating unit. The indicating unit may comprise any optical, tactile, and/or acoustical indication means. Use of a display, such as a display of a handheld device, for instance a smartphone or tablet computer, is preferred. For instance respiratory effort may be represented by a number ranging from 1 to 10, wherein 1 for example designates for example essentially unobstructed or extremely low respiratory effort and 10 extremely high respiratory effort. The same may be also obtained by using symbols, such as smileys, and/or description by words or short sentences, such as "low, medium, high". Still another possibility is displaying the percentage of maximum inspiratory effort, such as EMG % max, or using an arbitrary unit.

The indicating unit may also provide indicators for the posture signal, breathing signal, electromyography signals, movement signal, and heart rate signal but is not limited thereto. The indicating unit may be further adapted to provide an alarm if the posture of the subject is not correct. In addition, the accelerometer may be coupled with a couch or upper part of a bed and provides information about correct positioning of the patient to an electrical engine adapted for moving the couch or bed to the desired position. In addition or alternatively, an alarm may be provided in case the respiration effort is not within a predetermined range.

According to another embodiment of the invention the device comprises an indicating unit, wherein the indicating unit is configured to indicate the posture signal of the subject by indicating the position of the subject relative to an axis vertical to the ground. As indicated above, this may be performed by indicating an angle between the upper part of the body with respect to the ground.

According to another aspect of the present invention an electromyography patch for determining and/or monitoring the respiratory effort of a subject is provided. The patch comprises a first contacting electrode and a second contacting electrode, the first contacting electrode and the second contacting electrode coupled to the patch and adapted for contacting the skin of the subject; and at least one accelerometer, wherein a distance between the first electrode and the second electrode corresponds to a distance between a right parasternal location of the subject and a left parasternal location of the subject.

The electromyography patch is a single patch, i.e. the two electrodes are arranged on the same patch. The two contacting electrodes are space apart and embedded in isolating material, preferably material forming the patch. The patch may be made as indicated above. The same holds true for the accelerometer and/or other parameters characterizing the patch. The use of a single patch provides the additional advantage that correct positioning of the patch is facilitated. First, there is only the need to arrange a single patch instead of two. In addition, electrical (ECG) signals from the heart may be used as indicator for correct positioning of the single patch. The first contacting electrode and the second contacting electrode are preferably attached to the patch.

The second distance between a right parasternal location of the subject and a left parasternal location of the subject is the optimal distance between the two contacting electrodes for assessing the respiratory effort using for instance the proposed device or proposed method. Preferably, the distance is the distance of the electrodes placed one centimeter lateral to the left sternal border and the right sternal border of the subject. It will be appreciated that the distance between the two electrodes differs between different subjects, for instance it is larger for a full-grown person and smaller for an underage person, or infant. The distance may be in the range of two to eight centimeters, preferably in the range of four to six centimeters.

According to another embodiment of the present invention the proposed method further comprises receiving a movement signal of the subject, wherein determining the electromyography signal is further based on the movement signal.

According to still another embodiment of the present invention the method further comprises receiving a heart rate signal, and correcting the determined electromyography signal based on the heart rate signal and to derive the respiratory effort based on the corrected determined electromyography signal.

According to an embodiment of the present invention the electromyography signal is determined in the case the breathing signal is indicative of inspiration of the subject and the posture signal is indicative of a particular position of the subject relative to an axis vertical to the ground. As indicated above, such a particular position may encompass an angle, such as 45 degrees, with or without deviation.

According to another embodiment of the present invention, the method is used for monitoring/assessment of a respiratory disorder. Alternatively, the method may be used for monitoring/assessment of COPD and/or asthma. Still alternatively, the method may be also used for the diagnosis of a respiratory disorder, including for instance COPD and asthma.

COPD may be characterized by a particular respiratory effort and/or neural respiratory drive which may be determined from EMG signals making use of the proposed method or device.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
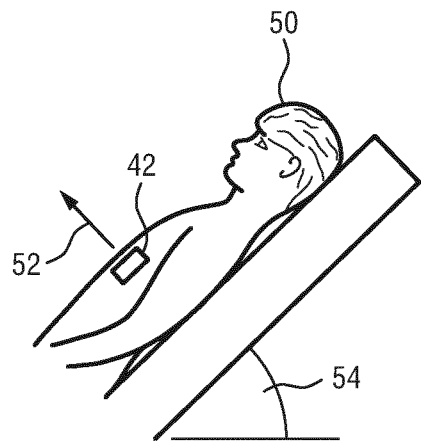
FIG. 1 shows a schematic drawing of a subject having the correct posture for determining the respiratory effort.

FIG. 1 schematically shows a subject 50 or patient having an EMG patch 42 on its chest, preferably at a second intercostal space symmetrically with respect to the sternum for measuring parasternal muscle activity. The upper part of the body of subject 50 is placed in a correct position for determining the respiratory effort, wherein the angle 54 with respect to an axis vertical to the ground is 45 degrees according to this exemplary embodiment.

Figure 2:
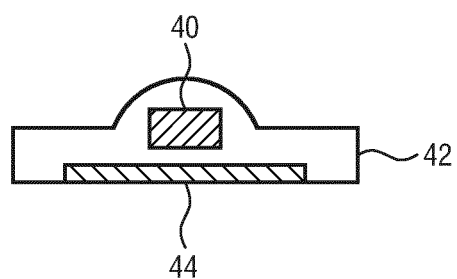
FIG. 2 shows a cross section through an embodiment of a proposed EMG patch for use in the device and method according to the present invention.

FIG. 2 is a cross section through an EMG patch which may be used for performing the proposed method and in connection with the proposed device 10. EMG patch 42 has a contacting surface to the human skin, wherein an electrical contact area 44 of patch 42 provides electrical contact to the skin of the subject 50. Patch 42 has further an accelerometer sensor 40 positioned in the center of the patch 42, above and spaced apart from the electrical contact area 44. One side of the contact area 44 is presented to the skin of the user 50, whereas the other side of the contact area 44 and accelerometer sensor 40 are watertightly embedded in silicone rubber material.

Figure 3:
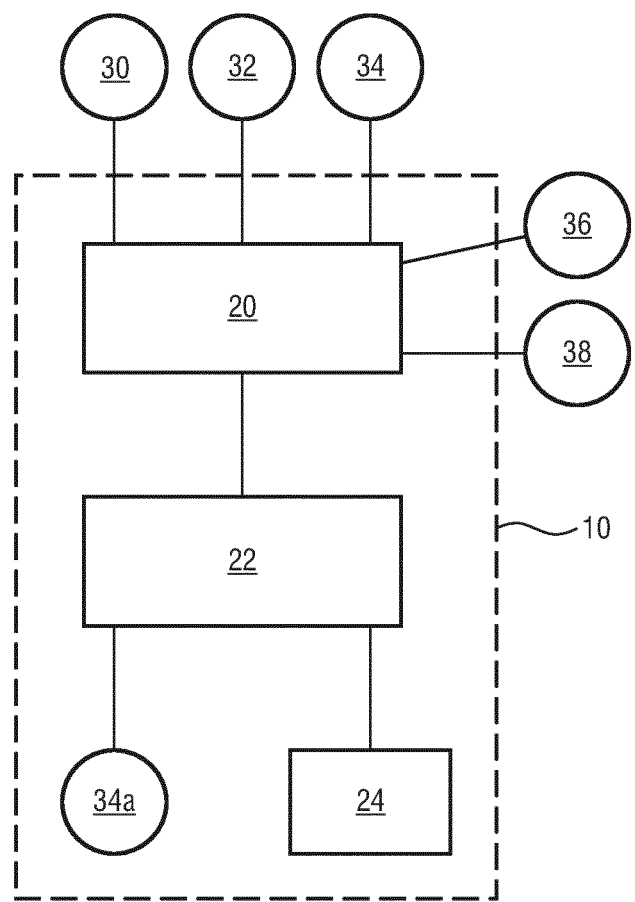
FIG. 3 schematically shows an embodiment of a device according to the present invention for monitoring the respiratory effort of a subject.

FIG. 3 schematically shows an embodiment of the device 10 for determining the respiratory effort according to the present invention. The device 10 comprises a receiving unit 20 for receiving a posture signal 30, a breathing signal 32, and an electromyography signal 34, 34a of the subject. Signals 30, 32, and 34 may be received from patch 42 shown in FIG. 2. In particular, posture signal 30 and breathing signal 32 are received from the accelerometer 40 and the electromyography signal 34 is received from the electrical contact area 44. Optionally a possible movement signal 36, and the heart rate signal 38 of the subject 50 are also received. The receiving unit 20 transmit the signals to a processing unit 22, which is configured to determine electromyography signal 34, 34a based on the posture signal and a breathing signal. Optionally, the electromyography signal 34a is also determined on the basis of the movement signal 36 which means that subject 50 does not move but remains quiescent. The heart rate signal 38 may be also employed for correcting the determined electromyography signal 34a. For this purpose, the effect of the heart rate signal is removed from the electromyography signal. In a next step the determined electromyography signal 34a representing activity of the parasternal muscle only, i.e. which is essentially free from disturbing signals arising from wrong posture, wrong time of subject's breathing cycle, any movement not related to breathing, and optionally artefacts from heartbeat. The determined electromyography signal may be taken as a direct measure of the respiratory effort, i.e. it represents a proportional value. The determined electromyography signal may be further used to calculate normalized neural respiratory drive.

Figure 4:
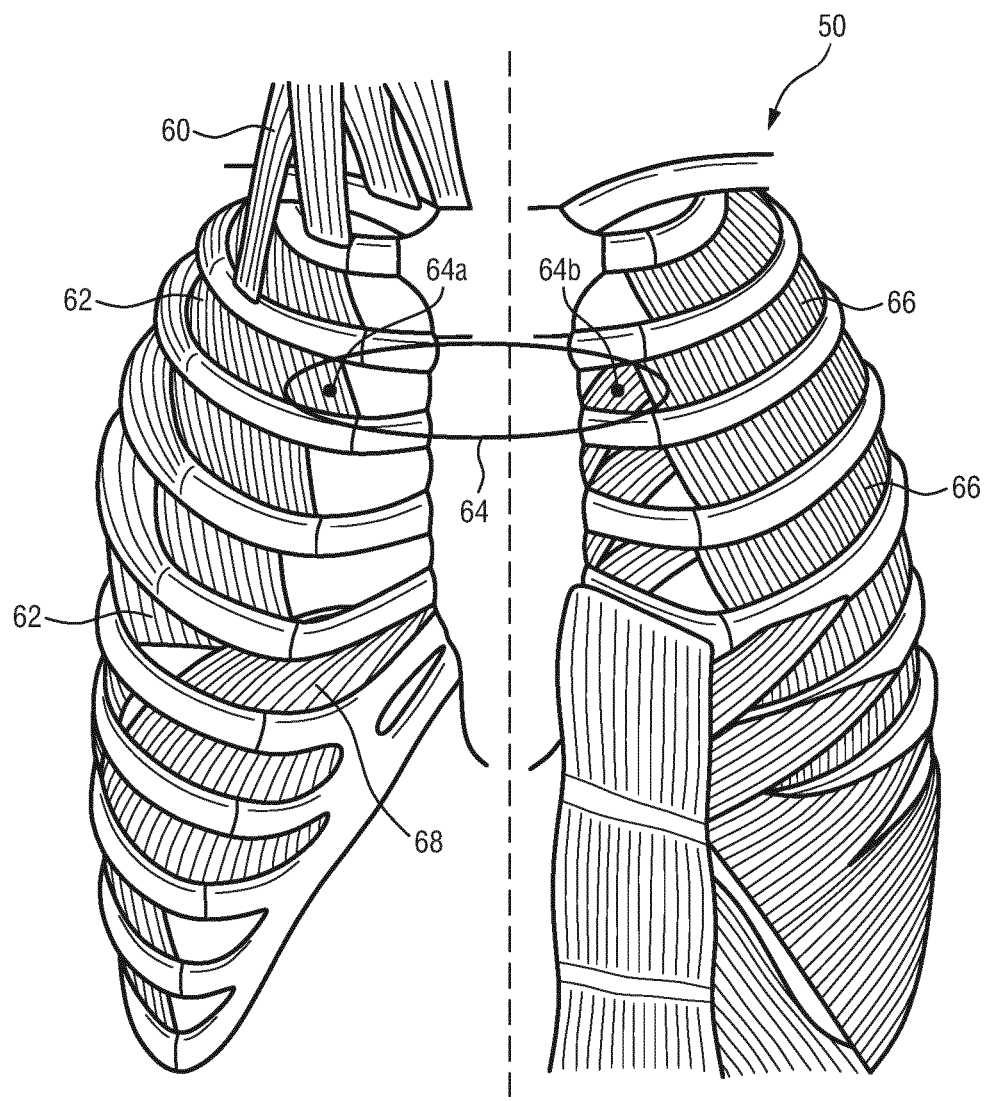
FIG. 4 shows an overview of intercostal spaces of the human body.

FIG. 4 shows a schematic overview of intercostal spaces of subject 50. The left side shows external intercostal muscles 62 required for inhalation. The right side indicates internal intercostal muscles 66 required for exhalation. Accordingly, external intercostals 62 are only shown on the left side and internal intercostals 66 are only shown on the right side of FIG. 4. From this overview further position of scalenes 60 and diaphragm 68 may be derived. Preferred placement position for an electromyography patch is indicated by reference number 64, wherein 64a and 64b represent the two positions for contacting areas 44 of patch 42 to be placed at a second intercostal space, preferably symmetrically with respect to the sternum of patient 50. The right position 64b is not properly shown due to indication of internal intercostals 66 only. A single patch 42 may be used wherein the dimensions of the patch 42 correspond essentially to the borders of placement position 64 and the two points 64a and 64b indicate the position of contacting electrodes 44. The distance between 64a and 64b is the preferred distance for placing a single patch 42 with two contacting electrodes 44 or two patches 42 with one contacting electrode 44, respectively, particularly the right parasternal location and a left parasternal location of the subject 50.

In conclusion, the device and method presented herein reliably monitor respiratory effort of a subject. As an advantage, taking a posture signal and a breathing signal of the subject into account enable determining of a more accurate and reliable EMG signal. In addition, variability, an important confounder in serial EMG analysis where EMGs of the same individual, but taken at different times, is therefore reduced.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for determining a respiratory effort of a subject, the device comprising:
   a receiver configured to receive a posture signal indicating at least one position of the subject, a breathing signal indicating breathing cycles of the subject, and an electromyography signal indicating neuronal activity of the subject, wherein the electromyography signal is measured independently of the posture signal and the breathing signal; and
   a processor configured to determine the electromyography signal for determining the respiratory effort of the subject that is received based on only when the received posture signal indicates a predetermined semi-recumbent position within a range from approximately 40 to 60 degrees relative to an axis vertical to the ground or a sitting position of the at least one position of the subject and the received breathing signal indicates a predetermined point/interval of an inhalation stage of the breathing cycles cycle of the subject, wherein the predetermined semi-recumbent position or sitting position and the predetermined point/interval of the inhalation stage are based on repeated daily measurements, wherein the processor is further configured to derive the respiratory effort from at least one of an analysis or an interpretation of the determined electromyography signal; and an indicator, wherein the indicator is configured to indicate the posture signal of the subject by indicating the at least one position of the subject relative to the axis vertical to the ground, and further configured to provide an alarm if the position of the subject does not fall within the predetermined semi-recumbent position within the range from approximately 40 to 60 degrees relative to the axis vertical to the ground or the sitting position and/or if the respiratory effort is not within a predetermined range.

2. The device according to claim 1, further comprising an accelerometer sensor for measuring the posture signal and the breathing signal of the subject.

3. The device according to claim 1, further comprising an electromyography patch for measuring the electromyography signal of the subject.

4. The device according to claim 3, wherein the electromyography patch is watertight.

5. The device according to claim 1, further comprising a plurality of electromyography patches for selectively measuring the electromyography signal of the subject.

6. The device according to claim 1,
wherein the receiver is further configured to receive a movement signal indicating at least one of a presence or an absence of non-breathing activity of the subject; and
wherein the processor is further configured to determine the electromyography signal for determining the respiratory effort of the subject that is received based on only when the received posture signal indicates the predetermined semi-recumbent position or sitting position of the at least one position of the subject, the received breathing signal indicates the predetermined point/interval of the inhalation stage of the breathing cycles of the subject and the received movement signal indicates the absence of non-breathing activity of the subject.

7. The device according to claim 1,
wherein the receiver is further configured for receiving a heart rate signal; and
wherein the processor is further configured to correct the determined electromyography signal based on the heart rate signal and
wherein the derivation of the respiratory effort is based on the corrected determined electromyography signal.

8. The device according to claim 1, wherein the received posture signal indicates a predetermined semi-recumbent position within the range from approximately 40 to 50 degrees.

9. The device according to claim 1, wherein the received posture signal indicates a predetermined semi-recumbent position within the range from approximately 41 to 49 degrees.

10. The device according to claim 1, wherein the received posture signal indicates a predetermined semi-recumbent position of approximately 45 degrees.

11. A method for determining a respiratory effort of a subject, the method comprising:
receiving a posture signal indicating at least one position of the subject, a breathing signal indicating breathing cycles of the subject, or an electromyography signal indicating neuronal activity of the subject, wherein the electromyography signal is measured independently of the posture signal and breathing signal;
determining the electromyography signal for determining the respiratory effort of the subject that is received based on only when the received posture signal indicates a predetermined semi-recumbent position within a range from approximately 40 to 60 degrees relative to an axis vertical to the ground or a sitting position of the at least one position of the subject and the received breathing signal indicates a predetermined point/interval of an inhalation stage of the breathing cycles of the subject, wherein the predetermined semi-recumbent position or sitting position and the predetermine point/interval of the inhalation stage are based on repeated daily measurements;
adjusting the position of the subject if not within the predetermined range or in a sitting position;
deriving the respiratory effort from at least one of an analysis or an interpretation of the determined electromyography signal; and
assessing whether the derived respiratory effort is indicative of a respiratory disorder.

12. The method according to claim 11, further comprising receiving a movement signal indicating at least one of a presence or an absence of non-breathing activity of the subject, and determining the electromyography signal for determining the respiratory effort of the subject that is received based on only when the received posture signal indicates the predetermined semi-recumbent position or a sitting position of the at least one position of the subject and the received breathing signal indicates the predetermined point/interval of the inhalation stage of the breathing cycles of the subject, and the movement signal indicates the absence of non-breathing activity of the subject.

13. The method according to claim 11, further comprising:
receiving a heart rate signal; and
correcting the determined electromyography signal based on the heart rate signal; and
wherein the deriving of the respiratory effort is based on the corrected determined electromyography signal.

14. The method according to claim 11, further comprising monitoring a respiratory disorder based on the derived respiratory effort of the subject.

15. A non-transitory computer readable medium comprising a computer program including program code for causing a computer or a processor to carry out the steps of the method as claimed in claim 11 when said computer program is carried out on the computer or the processor.

16. The method according to claim 11, wherein the received posture signal indicates a predetermined semi-recumbent position within the range from approximately 40 to 50 degrees.

17. The method according to claim 11, wherein the received posture signal indicates a predetermined semi-recumbent position within the range from approximately 41 to 49 degrees.

18. The method according to claim 11, wherein the received posture signal indicates a predetermined semi-recumbent position of approximately 45 degrees.

\* \* \* \* \*